(12) United States Patent
Kato et al.

(10) Patent No.: US 7,241,925 B2
(45) Date of Patent: Jul. 10, 2007

(54) METHOD FOR PRODUCING HALOGEN-SUBSTITUTED AROMATIC ALDEHYDE

(75) Inventors: Kinji Kato, Okayama (JP); Junya Nishiuchi, Okayama (JP); Mitsuharu Kitamura, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/011,136

(22) Filed: Dec. 15, 2004

(65) Prior Publication Data
US 2005/0143605 A1 Jun. 30, 2005

(30) Foreign Application Priority Data
Dec. 15, 2003 (JP) ............................. 2003-416630
Dec. 15, 2003 (JP) ............................. 2003-416631

(51) Int. Cl.
*C07C 45/49* (2006.01)
(52) U.S. Cl. ........................ 568/428; 568/437
(58) Field of Classification Search ................ 568/428, 568/437
See application file for complete search history.

(56) References Cited

U.S. PATENT DOCUMENTS 2,485,237 A    10/1949  Gresham et al.
4,588,844 A *   5/1986  Kysela et al. ................. 568/41
5,068,450 A *  11/1991  Crochemore et al. ........ 568/435
6,300,525 B1* 10/2001  Anderson et al. ............ 568/428
6,455,739 B1*  9/2002  Karseboom et al. ........ 568/437

FOREIGN PATENT DOCUMENTS

WO    WO 02/20447 A1    3/2002
WO    WO 03/022788 A1   3/2003

OTHER PUBLICATIONS

European Search Report, for Application No. EP 04 10 6385, dated Mar. 4, 2005, 4 pp.

* cited by examiner

*Primary Examiner*—Sikarl A. Witherspoon
(74) *Attorney, Agent, or Firm*—Antonelli, Terry, Stout & Kraus, LLP.

(57) ABSTRACT

In the production method of the invention, a halogen-substituted aromatic compound is reacted with carbon monoxide in the presence of hydrogen fluoride and boron trifluoride into a corresponding halogen-substituted aromatic aldehyde. By the use of hydrogen fluoride and boron trifluoride, the para position to halogen atom is selectively formylated to provide the halogen-substituted aromatic aldehyde in high yields in a short reaction time even at temperatures lower than room temperature.

10 Claims, No Drawings

METHOD FOR PRODUCING HALOGEN-SUBSTITUTED AROMATIC ALDEHYDE

BACKGROUND OF THE INVENTION

1. Field of the Invention

The present invention relates to a method for producing a halogen-substituted aromatic aldehyde, particularly p-fluorobenzaldehyde and a halogen-substituted aromatic aldehyde simultaneously having a halogen atom and a hydrocarbon group each being bonded directly to the aromatic ring, which is useful as raw materials for dyes, perfumes, medicines, agricultural chemicals, and additives for resins.

2. Description of the Prior Art

The production method of aromatic aldehydes by the formylation of aromatic hydrocarbons with carbon monoxide in the presence of a catalyst such as hydrogen chloride-aluminum chloride has been well known as Gattermann Koch reaction. This reaction, however, proceeds smoothly only when the aromatic hydrocarbon is substituted by an electron donating group such as alkyl group, but, proceeds slowly when the aromatic hydrocarbon is substituted by an electron attracting group to make the industrial use thereof difficult.

For example, U.S. Pat. No. 6,300,525 B1 discloses that p-fluorobenzaldehyde is produced by the reaction of fluorobenzene with carbon monoxide in the presence of a catalyst system comprising aluminum chloride and a very small amount of hydrogen chloride. However, even after 18 h of the reaction, the yield of p-fluorobenzaldehyde is as extremely low as about 24.1% on the basis of the aluminum chloride catalyst used, and as extremely low as 3.4% on the basis of the starting fluorobenzene (Example 4). The document teaches that the reaction can be promoted by 4-methylanisole. However, even after 89 h of the reaction in the presence of 4-methylanisole, the reported yield is 64.3% on the basis of the molar amount of aluminum chloride after subtracting the molar amount of 4-methylanisole added (probably because 4-methylanisole and aluminum chloride form a 1:1 complex), 29.7% on the basis of the molar amount of aluminum chloride when not subtracting the molar amount of 4-methylanisole, and 9.4% on the basis of the starting fluorobenzene. Since U.S. Pat. No. 6,300,525 B1 is silent as to by-products in the descriptions of examples, the types and the amounts of by-products produced are unknown.

U.S. Pat. No. 6,455,739 B1 discloses that p-fluorobenzaldehyde is produced by the reaction of fluorobenzene with carbon monoxide at 45 to 100° C. in the presence of an aluminum chloride-hydrogen chloride catalyst system. Although the document does not provide the numerical yield of p-fluorobenzaldehyde, it can read from FIG. 5 as about 74% yield on the basis of aluminum chloride, and about 58% conversion, about 91.1% selectivity and about 53% yield on the basis of fluorobenzene in case of an initial load of aluminum chloride and fluorobenzene of 50:50 which is taught to be preferred. U.S. Pat. No. 6,455,739 B1 teaches that o-fluorobenzaldehyde, m-fluorobenzaldehyde, chlorobis(fluorophenyl)methane and oligomers are by-produced and the production ratio of three fluorobenzaldehyde isomers is o-isormer:m-isomer:p-isomer=1.8:0.2:98.3.

Alternatively to Gattermann Koch reaction, U.S. Pat. No. 5,068,450 discloses to produce p-fluorobenzaldehyde by the reaction of fluorobenzene with methyl formate in the presence of a hydrogen fluoride/boron trifluoride catalyst. However, since the by-production of methanol is expected in the proposed method, there is a problem of difficult separation of the by-produced methanol from hydrogen fluoride and boron trifluoride.

U.S. Pat. No. 4,588,844 discloses that p-fluorobenzaldehyde is produced by the reaction of urotropin with fluorobenzene in the presence of hydrogen fluoride. In the proposed reaction, however, a considerable amount of o-fluorobenzaldehyde is by-produced and the total yield of o- and p-fluorobenzaldehydes is as extremely low as about 30%.

U.S. Pat. No. 6,300,525 B1 mentioned above further discloses that 2-fulorotoluene, 3-fluorotoluene, etc. are converted into corresponding aldehydes by the reaction with carbon monoxide in the presence of a catalyst system comprising aluminum chloride and a very small amount of hydrogen chloride. The document teaches in the working example that 2-fluorotoluene is converted into 4-fluoro-3-methylbenzene by the reaction with carbon monoxide at 60° C. for 20 h in a yield of about 67.4% on the basis of aluminum chloride used. The calculated yield on the basis of the starting 2-fluorobenzene is only about 11%.

Thus, in known methods, the halogen-substituted aromatic aldehydes are produced only in low yields despite a long reaction time, resulting in a low production efficiency and increasing production costs. In the reaction using the hydrogen chloride-aluminum chloride catalyst system, the reaction product mixture is usually treated with water after the formylation to separate the products and the catalyst, this making the regeneration of catalyst extremely difficult. Since a large amount of waste materials is produced by hydrolysis, the disposal thereof is quite costly.

SUMMARY OF THE INVENTION

As described above, the methods hitherto known are not suitable for the industrial production of the halogen-substituted aromatic aldehyde by directly introducing an aldehyde group into the halogen-substituted aromatic compound because of several problems: the yield is low even after a long-term reaction, and the catalyst cannot be reused because the separation of the catalyst from the products is difficult, thereby increasing production costs.

Thus, an object of the invention is to provide an industrially advantageous method for producing a halogen-substituted aromatic aldehyde by directly introducing an aldehyde group into a halogen-substituted aromatic compound.

The inventors have made extensive research on the production of a halogen-substituted aromatic aldehyde by directly introducing an aldehyde group into a halogen-substituted aromatic compound. As a result, it has been found that the halogen-substituted aromatic compound is converted into the corresponding halogen-substituted aromatic aldehyde in a short period of time with a high conversion, extremely high selectivity, high yield and high purity even at temperatures lower than room temperature, when the halogen-substituted aromatic compound is reacted with carbon monoxide in the presence of a catalyst comprising hydrogen fluoride and boron trifluoride. It has been further found that hydrogen fluoride and boron trifluoride used as the catalyst can be easily recovered and reused to render the process industrially very advantageous. The invention has been accomplished on the basis of these findings.

Thus, the present invention provides a method for producing a halogen-substituted aromatic aldehyde comprising a step of converting a halogen-substituted aromatic compound represented by the following formula 1:

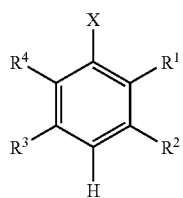

wherein $R^1$, $R^2$, $R^3$ and $R^4$ are the same or different and each represents hydrogen atom or aliphatic hydrocarbon group having 1 to 6 carbon atoms, X is fluorine atom when $R^1$, $R^2$, $R^3$ and $R^4$ are all hydrogen atom, and X is halogen atom selected from the group consisting of fluorine atom, chlorine atom, bromine atom and iodine atom when at least one of $R^1$, $R^2$, $R^3$ and $R^4$ is the aliphatic hydrocarbon group, into the halogen-substituted aromatic aldehyde represented by the following formula 2:

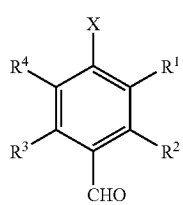

wherein X, $R^1$, $R^2$, $R^3$ and $R^4$ are the same as defined in the formula 1, by a reaction with carbon monoxide in the presence of hydrogen fluoride and boron trifluoride.

According to the method of the invention, a highly pure halogen-substituted aromatic aldehyde is cheaply produced from a halogen-substituted aromatic compound in high selectivity and high yield by a single step reaction.

DETAILED DESCRIPTION OF THE INVENTION

The starting halogen-substituted aromatic compound represented by the formula 1:

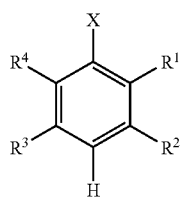

has a fluorine atom or has an aliphatic hydrocarbon group in addition to a halogen atom on the benzene ring, and has a hydrogen atom at the para position of the halogen atom.

$R^1$, $R^2$, $R^3$ and $R^4$ are the same or different and each represents hydrogen atom or aliphatic hydrocarbon group having 1 to 6 carbon atoms. The aliphatic hydrocarbon group is selected from methyl group, ethyl group, propyl group, butyl group, pentyl group, hexyl group and their isomeric groups, with methyl group being particularly preferred.

X is fluorine atom when $R^1$, $R^2$, $R^3$ and $R^4$ are all hydrogen atom. When at least one of $R^1$, $R^2$, $R^3$ and $R^4$ is the aliphatic hydrocarbon group, X is a halogen atom selected from the group consisting of fluorine atom, chlorine atom, bromine atom and iodine atom, with fluorine atom and chlorine atom being preferred.

Examples the halogen-substituted aromatic compound of the formula 1 include fluorine-substituted aromatic compounds such as monofluorobenzene, 2-fluorotoluene, 3-fluorotoluene, 2-fluoroethylbenzene, 3-fluoro-o-xylene, 2-fluoro-m-xylene, 5-fluoro-m-xylene and 2-fluoro-p-xylene; chlorine-substituted aromatic compounds such as 2-chlorotoluene, 3-chlorotoluene, 3-chloro-o-xylene and 2-chloro-p-xylene; bromine-substituted aromatic compounds such as 2-bromotoluene and 2-bromo-p-xylene; and iodine-substituted aromatic compounds such as 2-iodotoluene.

In the formylation of these halogen-substituted aromatic compounds in the presence of the catalyst comprising hydrogen fluoride and boron trifluoride, the para position to the halogen atom rather than the para position to the aliphatic hydrocarbon group is attacked by carbon monoxide to form the aldehyde. Therefore, the para position to the halogen atom should be a hydrogen atom.

In the present invention, it is important to carry out the reaction of the halogen-substituted aromatic compound with carbon monoxide (formylation) in the presence of the catalyst comprising hydrogen fluoride and boron trifluoride. By the use of such a catalyst, extremely high production efficiency can be achieve because the corresponding halogen-substituted aromatic aldehyde is produced in extremely high yields even in a short reaction time at a reaction temperature lower than room temperature. When the halogen-substituted aromatic compound is monofluorobenzene, the selectivity to p-fluorobenzaldehyde is extremely high, and the production of o-fluorobenzaldehyde isomer is minimized and the production of m-fluorobenzaldehyde isomer is completely prevented. Since hydrogen fluoride and boron trifluoride are highly volatile, the catalyst used can be easily recovered for reuse. Therefore, the disposal of used catalyst is avoided to make the process economical and reduce the load on the environments.

The amount of hydrogen fluoride to be used is preferably 5.0 mol or more, more preferably 7.0 mol or more per one mole of the starting halogen-substituted aromatic compound. The conversion of the starting halogen-substituted aromatic compound becomes high as the amount of hydrogen fluoride increases. However, since the use of an excessively large amount reduces the volume efficiency of production apparatus and increases the amount of hydrogen fluoride to be recovered, the upper limit of the amount to be used is preferably 30.0 mol per one mole of the starting halogen-substituted aromatic compound.

The amount of boron trifluoride to be used is preferably 1.1 to 5.0 mol, more preferably 1.2 to 3.5 mol per one mole of the starting halogen-substituted aromatic compound. If less than 1.1 mol, the rate of formylation is extremely decreased to make the process industrially disadvantageous. The amount of boron trifluoride to be used may exceed 5.0 mol. However, since the pressure of the reaction system reaches high level even before supplying carbon monoxide and further increases by supplying carbon monoxide, a reactor which is resistant to a considerably high pressure is unfavorably required. When the halogen-substituted aromatic compound is monofluorobenzene, the amount of boron trifluoride to be used is preferably 1.3 to 5.0 mol, more preferably 1.5 to 3.5 mol per one mole of the starting fluorobenzene.

The reaction temperature is an important process factor to prevent unfavorable side reactions, and the method of the invention is carried out preferably at 10° C. or lower, more preferably at 0° C. or lower, and still more preferably at −10° C. or lower. By the use of the catalyst comprising hydrogen fluoride and boron trifluoride, the formylation of the halogen-substituted aromatic compound proceeds rapidly even at such lower temperatures. The aldehyde produced may react with the non-reacted starting halogen-substituted aromatic compound to form by-products. Therefore, the method of the invention in which the formylation is carried out at temperatures lower than room temperature is advantageous also in view of minimizing the by-products. An excessively low temperature is not needed and the formylation is conducted usually at about −40° C. or higher.

The partial pressure of carbon monoxide in the formylation is preferably 0.5 MPa or higher, more preferably 0.7 MPa or higher in view of the yield. A pressure higher than 3 MPa is economically undesirable and not needed.

Under the conditions described above, the formylation is generally conducted for 1 to 50 h.

After completing the formylation, a solution containing a complex of halogen-substituted aromatic aldehyde-hydrogen fluoride-boron trifluoride is obtained. By thermally decomposing the complex, for example, in the presence of an appropriate decomposition aid, the solution of complex is separated into a decomposition aid solution containing the halogen-substituted aromatic aldehyde and the non-reacted halogen-substituted aromatic compound, and the catalyst comprising hydrogen fluoride and boron trifluoride. The separated hydrogen fluoride and boron trifluoride are reused as the catalyst for the subsequent run of reaction without disposing. Since the decomposition aid solution scarcely contains by-products except for the non-reacted halogen-substituted aromatic compound, a purified halogen-substituted aromatic aldehyde is obtained by a simple purification method such as distillation. The non-reacted halogen-substituted aromatic compound is recovered and reused in the subsequent run of the reaction.

The invention will be described in more detail with reference to the examples. However, it should be noted that the scope of the invention is not limited thereto.

EXAMPLE 1

A 500-mL autoclave equipped with a stirrer, three upper inlets, one bottom outlet and a jacket for controlling the inner temperature was used as the formylation reactor.

After cooling the autoclave to −20° C. or lower by passing a cooling medium through the jacket, 150 g (7.5 mol) of hydrogen fluoride and 72.1 g (0.75 mol) of fluorobenzene were charged. Then, 101.7 g (1.5 mol) of boron trifluoride was added under stirring while controlling the temperature so as not to exceed −20° C.

After the addition of boron trifluoride, the inner temperature of the autoclave was lowered to −25° C. and carbon monoxide was introduced until the inner pressure reached 2 MPa while maintaining the temperature at −25° C. After stirring for one hour while maintaining the temperature at −25° C. and the pressure at 2 MPa, the reaction liquid mixture was poured into an iced water. After adding toluene and shaking thoroughly, the oil layer was separated. The oil layer was washed with water and analyzed by gas chromatography. The conversion of fluorobenzene was 37.1 mol %, and the selectivity to p-fluorobenzaldehyde was 99.8 mol %. The production ratio of p-fluorobenzaldehyde and o-fluorobenzaldehyde was 99.96:0.04 and m-fluorobenzaldehyde was not detected.

EXAMPLE 2

The reaction and the treatment of the reaction liquid mixture were carried out in the same manner as in Example 1 except for changing the initial charge to 100 g (5.0 mol) for hydrogen fluoride, 96.1 g (1.0 mol) for fluorobenzene and 135.6 g (2.0 mol) for boron trifluoride. The results of gas chromatography on the oil layer showed that the conversion of fluorobenzene was 20.3 mol % and the selectivity to p-fluorobenzaldehyde was 99.8 mol %. The production ratio of p-fluorobenzaldehyde and o-fluorobenzaldehyde was 99.96:0.04 and m-fluorobenzaldehyde was not detected.

EXAMPLE 3

The reaction and the treatment of the reaction liquid mixture were carried out in the same manner as in Example 1 except for changing the initial charge of boron trifluoride to 152.6 g (2.25 mol), the reaction temperature to −30° C. and the reaction time to 3 h. The gas chromatography on the oil layer showed that the conversion of fluorobenzene was 71.6 mol % and the selectivity to p-fluorobenzaldehyde was 99.9 mol %. The production ratio of p-fluorobenzaldehyde and o-fluorobenzaldehyde was 99.97:0.03 and m-fluorobenzaldehyde was not detected.

EXAMPLE 4

The reaction was carried out in the same manner as in Example 1 except for changing the initial charge to 200 g (10.0 mol) for hydrogen fluoride, 48.1 g (0.5 mol) for fluorobenzene and 101.7 g (1.5 mol) for boron trifluoride, the reaction temperature to −30° C. and the reaction time to 5 h. In the same manner as in Example 1, the reaction liquid mixture was treated and the oil layer was analyzed by gas chromatography. The conversion of fluorobenzene was 90.6 mol % and the selectivity to p-fluorobenzaldehyde was 99.9 mol %. The production ratio of p-fluorobenzaldehyde and o-fluorobenzaldehyde was 99.97:0.03 and m-fluorobenzaldehyde was not detected.

EXAMPLE 5

The reaction was carried out in the same manner as in Example 1 except for changing the initial charge to 200 g (10.0 mol) for hydrogen fluoride, 48.1 g (0.5 mol) for fluorobenzene and 67.8 g (1.0 mol) for boron trifluoride, the reaction temperature to 20° C. and the reaction time to 3 h. In the same manner as in Example 1, the reaction liquid mixture was treated and the oil layer was analyzed by gas chromatography. The conversion of fluorobenzene was 30 mol % and the selectivity to p-fluorobenzaldehyde was 97.0 mol %. The formation of high-boiling products attributable to the reaction between p-fluorobenzaldehyde and the starting fluorobenzene was confirmed.

EXAMPLE 6

A 500-mL autoclave equipped with a stirrer, three upper inlets, one bottom outlet and a jacket for controlling the inner temperature was used as the formylation reactor.

After cooling the autoclave to −20° C. by passing a cooling medium through the jacket, 150.0 g (7.5 mol) of hydrogen fluoride and 82.6 g (0.75 mol) of 2-fluorotoluene were charged. Then, 75.9 g (1.12 mol) of boron trifluoride was added under stirring while controlling the temperature so as not to exceed −20° C.

After the addition of boron trifluoride, carbon monoxide was introduced into the autoclave until the inner pressure reached 2 MPa while maintaining the inner temperature at −20° C. After stirring for one hour while maintaining the temperature at −20° C. and the pressure at 2 MPa, the reaction liquid mixture was poured into an iced water. After adding hexane and shaking thoroughly, the oil layer was separated. The oil layer was washed with water and analyzed by gas chromatography. The conversion of 2-fluorotoluene was 73.5 mol %, the selectivity to 4-fluoro-3-methylbenzaldehyde was 99.3 mol %, the selectivity to 3-fluoro-4-methylbenzaldehyde was 0.5 mol %, and the total selectivity to two isomers was 99.8 mol %.

EXAMPLE 7

The reaction and the treatment of the reaction liquid mixture were carried out in the same manner as in Example 6 except for changing the initial charge of boron trifluoride to 101.7 g (1.5 mol). The results of gas chromatography on the oil layer showed that the conversion of 2-fluorotoluene was 84.2 mol %, the selectivity to 4-fluoro-3-methylbenzaldehyde was 99.4 mol %, the selectivity to 3-fluoro-4-methylbenzaldehyde was 0.5 mol %, and the total selectivity to two isomers was 99.9 mol %.

EXAMPLE 8

The reaction and the treatment of the reaction liquid mixture were carried out in the same manner as in Example 6 except for changing the initial charge of boron trifluoride to 101.7 g (1.5 mol) and the reaction temperature to 0° C. The results of gas chromatography on the oil layer showed that the conversion of 2-fluorotoluene was 80.5 mol %, the selectivity to 4-fluoro-3-methylbenzaldehyde was 99.1 mol %, the selectivity to 3-fluoro-4-methylbenzaldehyde was 0.6 mol %, and the total selectivity to two isomers was 99.7 mol %.

EXAMPLE 9

The reaction and the treatment of the reaction liquid mixture were carried out in the same manner as in Example 6 except for changing the initial charge to 100.0 g (5.0 mol) for hydrogen fluoride and 110.1 g (1.0 mol) for 2-fluorotoluene. The results of gas chromatography on the oil layer showed that the conversion of 2-fluorotoluene was 57.8 mol %, the selectivity to 4-fluoro-3-methylbenzaldehyde was 99.3 mol %, the selectivity to 3-fluoro-4-methylbenzaldehyde was 0.5 mol %, and the total selectivity to two isomers was 99.8 mol %.

EXAMPLE 10

After cooling the autoclave of the same type as used in Example 6 to −20° C. by passing a cooling medium through the jacket, 150.0 g (7.5 mol) of hydrogen fluoride and 82.6 g (0.75 mol) of 3-fluorotoluene were charged. Then, 101.7 g (1.5 mol) of boron trifluoride was added under stirring while controlling the temperature so as not to exceed −20° C.

After the addition of boron trifluoride, the inner temperature of the autoclave was lowered to −25° C. and carbon monoxide was introduced into the autoclave until the inner pressure reached 2 MPa while maintaining the inner temperature at −25° C. After stirring for one hour while maintaining the temperature at −25° C. and the pressure at 2 MPa, the reaction liquid mixture was poured into an iced water. After adding hexane and shaking thoroughly, the oil layer was separated. The oil layer was washed with water and analyzed by gas chromatography. The conversion of 3-fluorotoluene was 90.8 mol %, the selectivity to 4-fluoro-2-methylbenzaldehyde was 96.7 mol %, the selectivity to 2-fluoro-4-methylbenzaldehyde was 3.2 mol %, and the total selectivity to two isomers was 99.9 mol %.

EXAMPLE 11

After cooling the autoclave of the same type as used in Example 6 to −20° C. by passing a cooling medium through the jacket, 120.0 g (6.0 mol) of hydrogen fluoride and 76.0 g (0.6 mol) of 2-chlorotoluene were charged. Then, 81.4 g (1.2 mol) of boron trifluoride was added under stirring while controlling the temperature so as not to exceed −20° C.

After the addition of boron trifluoride, the inner temperature of the autoclave was lowered to −30° C. and carbon monoxide was introduced into the autoclave until the inner pressure reached 2 MPa while maintaining the inner temperature at −30° C. After stirring for one hour while maintaining the temperature at −30° C. and the pressure at 2 MPa, the reaction liquid mixture was poured into an iced water. After adding hexane and shaking thoroughly, the oil layer was separated. The oil layer was washed with water and analyzed by gas chromatography. The conversion of 2-chlorotoluene was 18.0 mol %, the selectivity to 4-chloro-3-methylbenzaldehyde was 90.8 mol %, the selectivity to 3-chloro-4-methylbenzaldehyde was 8.8 mol %, and the total selectivity to two isomers was 99.6 mol %.

EXAMPLE 12

The reaction and the treatment of the reaction liquid mixture were carried out in the same manner as in Example 11 except for changing the starting compound to 3-chlorotoluene. The results of gas chromatography on the oil layer showed that the conversion of 3-chlorotoluene was 57.1 mol %, the selectivity to 4-chloro-2-methylbenzaldehyde was 75.8 mol %, the selectivity to 2-chloro-4-methylbenzaldehyde was 23.9 mol %, and the total selectivity to two isomers was 99.7 mol %.

EXAMPLE 13

After cooling the autoclave of the same type as used in Example 6 to −5° C. by passing a cooling medium through the jacket, 120.0 g (6.0 mol) of hydrogen fluoride and 84.4 g (0.6 mol) of 2-chloro-p-xylene were charged. Then, 81.4 g (1.2 mol) of boron trifluoride was added under stirring while controlling the temperature so as not to exceed −5° C.

After the addition of boron trifluoride, carbon monoxide was introduced into the autoclave until the inner pressure reached 2 MPa while maintaining the inner temperature at −5° C. After stirring for one hour while maintaining the temperature at −5° C. and the pressure at 2 MPa, the reaction liquid mixture was poured into an iced water. After adding hexane and shaking thoroughly, the oil layer was separated. The oil layer was washed with water and analyzed by gas chromatography. The conversion of 2-chloro-p-xylene was 78.5 mol % and the selectivity to 4-chloro-2,5-dimethylbenzaldehyde was 99.2 mol %.

What is claimed is:

1. A method for producing a halogen-substituted aromatic aldehyde comprising a step of converting a halogen-substituted aromatic compound represented by the following formula 1:

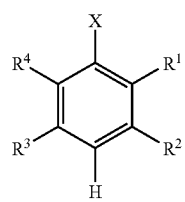

(1)

wherein $R^1$, $R^2$, $R^3$ and $R^4$ are the same or different and each represents hydrogen atom or aliphatic hydrocarbon group having 1 to 6 carbon atoms, X is fluorine atom when $R^1$, $R^2$, $R^3$ and $R^4$ are all hydrogen atom, and X is halogen atom selected from the group consisting of fluorine atom, chlorine atom, bromine atom and iodine atom when at least one of $R^1$, $R^2$, $R^3$ and $R^4$ is the aliphatic hydrocarbon group, hydrogen being in the para-position to X, into the halogen-substituted aromatic aldehyde represented by the following formula 2:

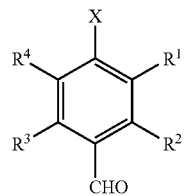

(2)

wherein X, $R^1$, $R^2$, $R^3$ and $R^4$ are the same as defined in the formula 1, the —CHO group, being in the para-position to X, by a reaction with carbon monoxide in the presence of hydrogen fluoride and boron trifluoride, wherein said converting is carried out at a reaction temperature of 0° C. or lower.

2. The method according to claim 1, wherein the halogen-substituted aromatic compound is fluorobenzene.

3. The method according to claim 2, wherein 5.0 to 30.0 mol of hydrogen fluoride and 1.3 to 5.0 mol of boron trifluoride are used per one mole of fluorobenzene.

4. The method according to claim 1, wherein at least one of $R^1$, $R^2$, $R^3$ and $R^4$ is the aliphatic hydrocarbon group.

5. The method according to claim 4, wherein 5.0 to 30.0 mol of hydrogen fluoride and 1.1 to 5.0 mol of boron trifluoride are used per one mole of the halogen-substituted aromatic compound.

6. The method according to claim 4, wherein X is chlorine atom or fluorine atom.

7. The method according to claim 1, wherein said halogen-substituted aromatic compound is converted into said halogen-substituted aromatic aldehyde in a single step reaction.

8. The method according to claim 1, wherein said halogen-substituted aromatic compound is selected from the group consisting of 2-fluorotoluene, 3-fluorotoluene, 2-fluoroethylbenzene, 3-fluoro-o-xylene. 2-fluoro-m-xylene. 5-fluoro-m-xylene, 2-fluoro-p-xylene, 2-chlorotoluene, 3-chloro-toluene, 3-chloro-o-xylene, 2-chloro-p-xylene, 2-bromotoluene, 2-bromo-p-xylene and 2-iodotoluene.

9. The method according to claim 1, wherein 7.0 to 30.0 mol of hydrogen fluoride and 1.2 to 3.5 mol of boron trifluoride are used per one mole of the halogen-substituted aromatic compound.

10. The method according to claim 1, wherein said reaction temperature is −10° C. or lower.

* * * * *